(12) United States Patent
Feng et al.

(10) Patent No.: US 12,669,426 B2
(45) Date of Patent: Jun. 30, 2026

(54) FLEXIBLE WALL DEVICE AND METHOD FOR MEASURING GAS PERMEABILITY COEFFICIENT AND GAS DIFFUSION COEFFICIENT OF SOIL

(71) Applicant: FUZHOU UNIVERSITY, Fuzhou (CN)

(72) Inventors: Song Feng, Fuzhou (CN); Shufu Huang, Fuzhou (CN); Liangtong Zhan, Fuzhou (CN); Hongwei Liu, Fuzhou (CN)

(73) Assignee: FUZHOU UNIVERSITY, Fuzhou (CN)

( * ) Notice: Subject to any disclaimer, the term of this patent is extended or adjusted under 35 U.S.C. 154(b) by 277 days.

(21) Appl. No.: 18/586,583

(22) Filed: Feb. 26, 2024

(65) Prior Publication Data

US 2024/0393224 A1    Nov. 28, 2024

(30) Foreign Application Priority Data

May 22, 2023    (CN) .......................... 202310578813.8

(51) Int. Cl.
G01N 15/08    (2006.01)
G01N 33/24    (2006.01)

(52) U.S. Cl.
CPC ..... G01N 15/0826 (2013.01); G01N 15/0806 (2013.01); G01N 33/24 (2013.01)

(58) Field of Classification Search
None
See application file for complete search history.

(56) References Cited

U.S. PATENT DOCUMENTS

2005/0041525 A1* 2/2005 Pugia ................ B01L 3/502746
366/341

FOREIGN PATENT DOCUMENTS

| CN | 1312466 | C |   | 4/2007 |   |   |
|---|---|---|---|---|---|---|
| CN | 106053317 | A |   | 10/2016 |   |   |
| CN | 108344668 | A |   | 7/2018 |   |   |
| CN | 105806766 | B |   | 1/2019 |   |   |
| CN | 109883892 | A |   | 6/2019 |   |   |
| CN | 111458274 | A | * | 7/2020 | ............. | G01N 13/04 |

(Continued)

*Primary Examiner* — Eric S. McCall
*Assistant Examiner* — Nigel H Plumb
(74) *Attorney, Agent, or Firm* — Bayramoglu Law Offices LLC

(57) ABSTRACT

A flexible wall device and method for measuring gas permeability coefficient and gas diffusion coefficient of unsaturated soil includes a gas washing device, a confining pressure-volume change system, a drying-wetting cycle control system and a gas measuring device. The drying-wetting cycle control system includes a humidity controller and valves. The gas measuring device includes a top lid, a cylindrical wall, a base, an upper chamber and a lower chamber. The top lid, the cylindrical wall and the base are connected by bolts and nuts, and the base has four passages, which are respectively connected to the gas washing device, the confining pressure-volume change system, the drying-wetting cycle control system and the gas measuring device, between the base and top lid are sequentially arranged from bottom to top as the lower chamber, lower perforated plate, lower permeable stone, sample, upper permeable stone, upper perforated plate, upper chamber, and control rod.

15 Claims, 3 Drawing Sheets

(56)     References Cited

FOREIGN PATENT DOCUMENTS

| CN | 113758850 | A | 12/2021 |
| CN | 111458274 | B | 3/2022 |

* cited by examiner

FLEXIBLE WALL DEVICE AND METHOD FOR MEASURING GAS PERMEABILITY COEFFICIENT AND GAS DIFFUSION COEFFICIENT OF SOIL

CROSS REFERENCE TO THE RELATED APPLICATIONS

This application is based upon and claims priority to Chinese Patent Application No. 202310578813.8, filed on May 22, 2023, the entire contents of which are incorporated herein by reference.

TECHNICAL FIELD

The present invention relates to a flexible wall device and a method for measuring gas permeability coefficients and gas diffusion coefficients of unsaturated soils under drying and wetting cycles.

BACKGROUND

Shallow soils in nature are usually in an unsaturated state, and quantifying gas transport in unsaturated soils is critical in many fields. The gas migration of unsaturated soil occurs through two main transport mechanisms: convection and diffusion, where the convection is influenced by the gas permeability coefficient ($k_a$) and gas pressure gradient of the soil, while the diffusion is influenced by the gas diffusion coefficient ($D_p$) and gas concentration gradient in the soil. Determination of gas permeability coefficient and gas diffusion coefficient of the soil is of great significance in soil and air pollution control, agriculture, etc. For example, the landfill gas (methane and carbon dioxide) produced by anaerobic degradation of organic components in landfills are mainly discharged to the atmosphere through convection under the action of the pressure difference between the top and base of landfill cover system. Moreover, in the agricultural field and vegetation slope protection, the oxygen consumption of plant roots is mainly transported from the atmosphere to the soil through diffusion. However, under the action of alternating rainfall and drying on the site, most of the topsoil undergoes multiple wetting and drying cycles, and during the wetting and drying process, the soil swells and shrinks, and the volume and microstructure of the soil have undergone significant changes, which significantly affects the gas permeability coefficient and gas diffusion coefficient of the soil.

At present, the measurement of the gas permeability coefficient and gas diffusion coefficient of the soil in the laboratory is mainly carried out through a rigid wall permeameter, that is, the side of the sample is connected to the rigid sleeve or rigid side wall, such as the patent CN108344668A "Experimental device for testing diffusion coefficient and osmotic coefficient of unsaturated dielectric gas", CN109883892A "Measurement device and method for diffusion coefficients of gas of unsaturated soils", CN106053317A "Unsaturated garbage soil bidirectional gas permeability coefficient determinator". The soil column devices are also used to measure the gas permeability coefficient and gas diffusion coefficient of unsaturated soil, such as the patent CN111458274B "Soil column device and method for measuring gas permeability coefficient and gas diffusion coefficient of unsaturated soil". When using either a rigid wall permeameter or a soil column device to measure the gas permeability coefficients and gas diffusion coefficients of unsaturated clays, the following limitations exist:

(1) gaps are likely to exist between the sample and the rigid wall, which can lead to preferential side-wall flow of gases along the interface between the sample and the rigid wall. Since the preferential side-wall flow of gas is much higher than gas flow passing through the sample, it significantly overestimates the gas transport parameters of the sample; (2) the compacted clay is commonly used as an impermeable material in landfill cover systems due to its low permeability and good airtightness; however, under the action of drying and wetting cycles, the clay sample is prone to shrinkage, which not only leads to the preferential sidewall flow of gases between the sample and the rigid wall, but also affects the pore structure of the soil sample, leading to changes in the gas permeability coefficient and gas diffusion coefficient. The rigid-wall devices are neither able to avoid the preferential sidewall flow of gases nor to quantify the volume change of soils under drying and wetting cycles, making them unsuitable for measuring gas permeability coefficients and gas diffusion coefficients of fine-grained soils under the action of drying and wetting cycles. These drawbacks can be overcome in a more controlled manner, such as by using a flexible wall permeameter.

Currently, although there are flexible wall permeameters to measure the saturated hydraulic conductivity ($k_s$) of soil, such as the patents CN113758850A "Flexible wall permeameter realizing integrated temperature-stress control under dry and wet cycling", CN1312466C "A flexible wall permeameter for measuring the coefficient of permeability", and CN105806766B "A flexible wall permeameter that can measure the body change"; and there are flexible wall permeameters to measure the gas permeability coefficient of unsaturated soil, but these flexible wall permeameters are not suitable for measuring gas diffusion coefficient, which is mainly due to the fact that the measurement principle of the gas diffusion coefficient is very different from that of the gas permeability coefficient, which requires the use of multiple chambers with tracer gases and the need to control the opening and closing of the different chambers during the test to control the concentration of tracer gases in different chambers. Currently, there is no flexible wall device for measuring the gas diffusion coefficient of unsaturated soil. In addition, most of the current measurements of the gas permeability coefficient and the gas diffusion coefficient are carried out using two independent devices, and the loading and unloading of the samples in different instruments are prone to disturbances such as sample breakage, which affects the measurement results, and the two sets of devices also raise the cost, cumbersome operation, and a long test cycle. Compared with the existing rigid-wall permeameters that measure the gas permeability coefficient and gas diffusion coefficient of unsaturated soils, there is no flexible-wall device that can overcome the preferential side-wall flow of gases and thus measure the gas permeability coefficient and gas diffusion coefficient of unsaturated soils.

SUMMARY

In order to overcome the problems of existing rigid wall devices, the present invention provides a flexible wall device and a method for measuring gas permeability coefficients and gas diffusion coefficients of unsaturated soils.

The technical solution of the present invention is:

The flexible wall device for measuring gas permeability coefficients and gas diffusion coefficients of unsaturated soils: it consists of a gas washing device, a confining pressure-volume change system, a drying-wetting cycle control system and a gas measuring device, the gas washing device includes a high-purity nitrogen cylinder, a pressure reducing valve, a pressure regulating valve and a steady-flow valve; the confining pressure-volume change system includes an air compressor, a pressure regulating valve I, a pressure regulating valve II and a volume change measuring tube; the drying-wetting cycle control system includes a humidity controller, a humidity controller valve I and a humidity controller valve II; the gas measuring device includes a top lid, a cylindrical wall, a base, an upper chamber and a lower chamber, the top lid, the cylindrical wall and the base are connected by bolts and nuts, and the base has four passages, which are respectively connected to the gas washing device, the confining pressure-volume change system, the drying-wetting cycle control system and the gas measuring device; between the base and top lid are sequentially arranged from bottom to top as the lower chamber, lower perforated plate, lower permeable stone, sample, upper permeable stone, upper perforated plate, upper chamber, and control rod.

The top lid, the cylindrical wall and the base enclosing a pressure chamber; the four passages of the base are respectively air inlet passage, air outlet passage, water inlet passage and base passage; the air inlet end of the air inlet passage is connected to the gas washing device and the air outlet end of the air inlet passage is connected to the upper chamber; the air inlet end of the air outlet passage is connected to the upper chamber and the air outlet end of the air outlet passage is connected to the drying-wetting cycle control system; a water inlet end of the water inlet passage is connected to the volume change measuring tube and the water outlet end of the water inlet passage is connected to the pressure chamber; the end of the base passage is connected to the lower chamber, and the other end of the base passage are respectively connected to the drying-wetting cycle control system and the confining pressure-volume change system.

The high-purity nitrogen cylinder is equipped with the pressure reducing valve, the pressure reducing valve is connected to the pressure regulating valve and the steady-flow valve arranged in series, and the steady-flow valve is connected to the air inlet end of the air inlet passage in the base.

The humidity controller of the drying-wetting cycle control system is connected to the base passage at one end and the air outlet passage at one other end, the humidity controller valve I is installed between the air outlet passage and the humidity controller, and the humidity controller valve II is installed between the base passage and the humidity controller.

The output end of the air compressor is connected to the pressure regulating valve I and the pressure regulating valve II set in parallel, an output end of the pressure regulating valve I is connected to one end of the volume change measuring tube, one other end of the volume change measuring tube is connected to the water inlet end of the water inlet passage of the base, and the water inlet passage is connected to the pressure chamber; the output end of the pressure regulating valve II is connected to the base passage of the base in turn via a U-shaped pressure measuring tube, a gas sampling port and a capillary tube II, the aforementioned base passage leads to the lower chamber, and the pressure regulating valve II is used to regulate the gas pressure in the lower chamber; a droplet of liquid is injected into the capillary tube II, so that the gases at both ends of the capillary are isolated from each other, but their air pressure is equal.

The exhaust valve and the control rod connected to a perforated loading plate at one end are installed at the top lid, the control rod rotatably runs through the top of the top lid and the upper chamber, and the perforated loading plate is connected to the lower end of the control rod and is located inside the upper chamber; the bottom of the upper chamber is sequentially equipped with the upper permeable stone and the upper perforated plate from the bottom to the top, a piece of perforated silicone gasket is formed between the upper perforated plate and the perforated loading plate, and the opening specifications of the perforated loading plate, the perforated silicone gasket, and the upper perforated plate are exactly the same, the perforated silicone gasket and the upper perforated plate are tightly bonded and placed according to the overlap of the opening parts, and the two openings do not block each other; the top of the lower chamber is equipped with the lower perforated plate and the lower permeable stone from bottom to top, a foundation is formed at the bottom of the lower chamber, the upper chamber and the lower chamber have the same internal net height.

The control rod seals a sealing ring I and the top lid through nut I, and the control rod seals a sealing ring II and the upper chamber through nut II.

The upper chamber is provided with two openings on its side-wall, and the two openings are connected to an air inlet pipe and an air outlet pipe, the air inlet pipe is connected to the air inlet passage of the base, the air outlet pipe is connected to the humidity controller, an electronic soap film flowmeter, a capillary tube I in turn through the air outlet passage, and a droplet is injected into the capillary tube I.

Another technical solution used in the present invention is: A method for measuring gas permeability coefficients and gas diffusion coefficients of unsaturated soils, including the following steps:

Step 1, preparation of sample: the soil to be measured is dried, crushed and sieved through a 2 mm sieve, the soil is adjusted to the target moisture content, and then compacted in layers with molds according to the target dry density, and the inter-layer interface is scraped.

Step 2, install the sample: place the lower chamber, the sample, and the upper chamber on the surface of the foundation from bottom to top, and then paste a thin layer of Vaseline on the outer walls of the foundation, the lower chamber and the upper chamber; and then wrap a latex film on the sidewalls of the foundation, the lower chamber, the sample and the upper chamber, and finally fix the two ends of the latex film on the foundation and the upper chamber respectively with O-rings I and O-rings II and then immediately followed by fixing and sealing the cylindrical wall, the base, and the top lid with nuts and bolts; open the exhaust valve, adjust the pressure regulating valve I, and apply a certain air pressure to the volume change measuring tube, so that water flows through the pipeline into the pressure chamber; until the exhaust valve discharges water and no air bubbles, close the exhaust valve; adjust the pressure regulating valve I, and apply a certain confining pressure (10-20 kPa) to the sample.

Step 3, flush the upper chamber: close all the valves, rotate the control rod, so that the openings on the perforated loading plate and the upper perforated plate just misaligned with each other, to isolate gas of the upper chamber from entering the sample through the upper perforated plate, and then open the high-purity nitrogen cylinder and the valve of the electronic soap film flowmeter, control the inlet flow rate through the adjustment of the pressure regulating valve and the steady-flow valve, and the gas flows into the upper chamber through the air inlet pipe, and is discharged into the atmosphere through the air outlet pipe; after 8-10 minutes, close the pressure reducing valve of the high-purity nitrogen cylinder and the valve of the electronic soap film flowmeter to stop the nitrogen input.

Step 4, open the capillary valve I and capillary valve II, rotate the control rod, so that the perforated loading plate and the upper perforated plate connect with each other through their respective openings, and the gas in the upper chamber can flow through the upper perforated plate into the sample, and immediately start the timer, this time t=0, and then determine the concentration of oxygen in the lower chamber over time through the gas sampling port which is connected to the lower chamber, for the sample with the degree of saturation <85%, the oxygen concentration in the lower chamber should be measured in minutes as a time scale, and for the sample with the degree of saturation ≥85%, the oxygen concentration in the lower chamber should be measured on a time scale of hours.

Step 5, the following theoretical equation derived from Fick's law is used to best-fit the oxygen concentration in the lower chamber with respect to time to determine the gas diffusion coefficient $D_p$:

$$D_P = -\frac{3H^2Lt\left[\ln B - \ln A + \ln\left(\frac{H}{2H+2L\varepsilon} - \frac{C_t}{C_0}\right)\right]}{3H - L\varepsilon} \quad (1)$$

$$\text{wherein: } A = -\frac{L\varepsilon}{H} - \frac{2L^2\varepsilon^2}{3H^2} \quad (2)$$

$$B = \left(\frac{L\varepsilon}{H} - \frac{L^2\varepsilon^2}{3H^2}\right)\left(\frac{5L\varepsilon}{3H} + 2\right) + \frac{L^3\varepsilon^3}{H^3} + \frac{L^2\varepsilon^2}{H^2} \quad (3)$$

wherein: t is the time; L is half of the height (m) of the sample; H is the internal net height (m; equal to the internal net height of the lower chamber) of the upper chamber; $C_0$ and $C_t$ are the oxygen concentration in the lower chamber at the beginning and the oxygen concentration ($m^3$ $m^{-3}$) in the lower chamber at the time of t; $\varepsilon$ is the gas-filled porosity of the sample ($m^3$ $m^{-3}$).

Step 6, the measurement of gas permeability coefficient: close the capillary valve I and capillary valve II, open the valve of the U-shaped pressure measuring tube and the valve of electronic soap film flowmeter, open the air compressor, adjust the inlet pressure through the pressure regulating valve II to apply a constant air pressure in the lower chamber, when the U-shaped pressure measuring tube readings become stabilized, record the U-shaped pressure measuring tube and electronic soap film flowmeter readings.

Step 7, the inlet pressure is changed to obtain the gas flow rates at three different air pressures, and the gas permeability coefficient of the soil sample can be calculated according to the following equation derived based on Darcy's law:

$$k_a = \frac{\mu Q h}{S\Delta P} \quad (4)$$

where S is the cross-sectional area of the sample; μ is the viscosity coefficient of the gas; ΔP is the pressure difference between the two ends of the sample; h is the height of the sample; Q is the outflow rate of the gas.

Step 8, close the valve of the U-shaped pressure measuring tube and the valve of electronic soap film flowmeter, open the humidity control valve I and humidity control valve II, adjust the humidity controller according to the target moisture content, and control the gas flow of constant humidity through the sample, equilibrate for 8-10 days, and repeat the fourth to the seventh steps, the gas permeability coefficient and the gas diffusion coefficient of the soil samples of different moisture contents are obtained; after each dry and wet cycle, the volume change measuring tube readings are recorded, and the volume change of the sample size is obtained.

The beneficial effects of the present invention are:

The present invention has developed a flexible wall device for measuring gas permeability coefficients and gas diffusion coefficients of unsaturated soils, which overcomes the following shortcomings of conventional rigid wall devices: measurement errors in gas diffusion coefficients due to preferential sidewall flow of gas, inability to simulate the stress state of soil samples in the field, and inability to measure the volume changes of samples caused by wetting and drying cycles. The present invention can avoid the preferential flow along the side wall of the sample caused by the sample shrinkage during the drying process by applying a confining pressure, can better simulate the stress state of the soil sample in the field, and can measure the volume change of the sample induced by the drying-wetting cycle as well as the gas permeability coefficient and the gas diffusion coefficient of the sample after the volume change of the sample, which can greatly enhance the measurement range and accuracy of the sample's gas permeability coefficient and the gas diffusion coefficient.

The present invention carries out drying-wetting cycle test through humidity control technology, and based on one sample, its gas permeability coefficient, gas diffusion coefficient and volume change under different water contents can be measured simultaneously. Combined with the flexible wall device mentioned above, it solves the problem that the gas permeability coefficient and gas diffusion coefficient of the soil under the action of drying and wetting cycle are difficult to be measured, and it is able to carry out multiple drying and wetting cycles, which can better simulate the real situation of the natural world, and overcome the limitation that the previous device needs multiple samples to carry out the measurements.

At present, most of the measurements of gas permeability coefficient and gas diffusion coefficient are carried out using two independent devices, which are costly, cumbersome and have a long test cycle. The present invention can complete the measurement of gas permeability coefficient and gas diffusion coefficient of the soil on the same sample, avoiding the disturbance to the soil sample due to multiple sample disassembling, and can effectively evaluate the correlation between the sample volume change and the gas permeability coefficient and gas diffusion coefficient.

BRIEF DESCRIPTION OF THE DRAWINGS

The invention is described in further detail below in connection with the accompanying drawings and specific embodiments.

In the Figure: 1—high-purity nitrogen cylinder; 2—pressure reducing valve; 3—pressure regulating valve; 4—steady-flow valve; 5—capillary tube I; 6—capillary valve I; 7—valve of electronic soap film flowmeter; 8—electronic soap film flowmeter; 9—air inlet passage; 10—air outlet passage; 11—nut; 12—bolt; 13—control rod; 14—nut I; 15—ring I; 16—exhaust valve; 17—top lid; 18—cylindrical wall; 19—pressure chamber; 20—nut II; 21—ring II; 22—air inlet pipe; 23—air outlet pipe; 24—upper chamber; 25—O-rings II; 26—perforated loading plate; 27—perforated silicone gasket; 28—upper perforated plate; 29—upper permeable stone; 30—sample; 31—lower permeable stone; 32—lower perforated plate; 33—latex film; 34—lower chamber; 35—foundation; 36—O-rings I; 37—base; 38—humidity controller valve I; 39—humidity controller; 40—water inlet passage; 41—base passage; 42—humidity controller valve II; 43—gas sampling port; 44—capillary valve II; 45—capillary tube II; 46—valve of the U-shaped pressure measuring tube; 47—U-shaped pressure measuring tube; 48—air compressor; 49—pressure regulating valve I; 50—pressure regulating valve II; 51—volume change measuring tube.

DETAILED DESCRIPTION OF THE EMBODIMENTS

In the description of the present invention, it is to be understood that the terms "vertical", "horizontal", "top", "bottom", "front", "back", "left", "right", "vertical", "horizontal", "top", "bottom", "inside", "outside", etc., indicate orientation or positional relationships based on the orientation or positional relationship shown in the accompanying drawings, and are only for the purpose of facilitating the description of the present invention, and are not intended to indicate or imply that the device or element referred to must be constructed and operated in a particular orientation, and are not to be construed as limitations on the invention.

Figure 1:
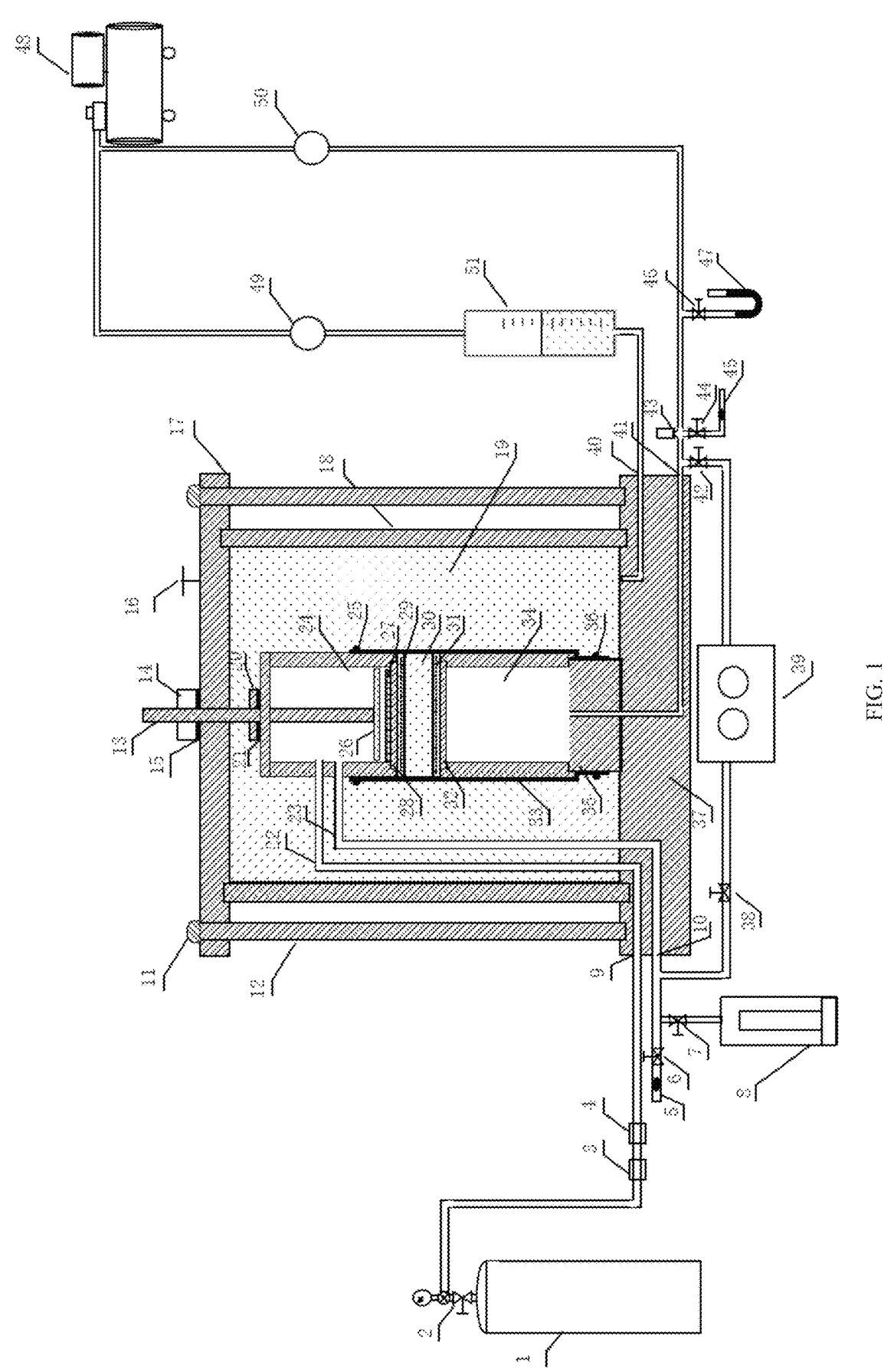
FIG. 1 is a schematic diagram of the general structure of the present invention.
Figure 2:
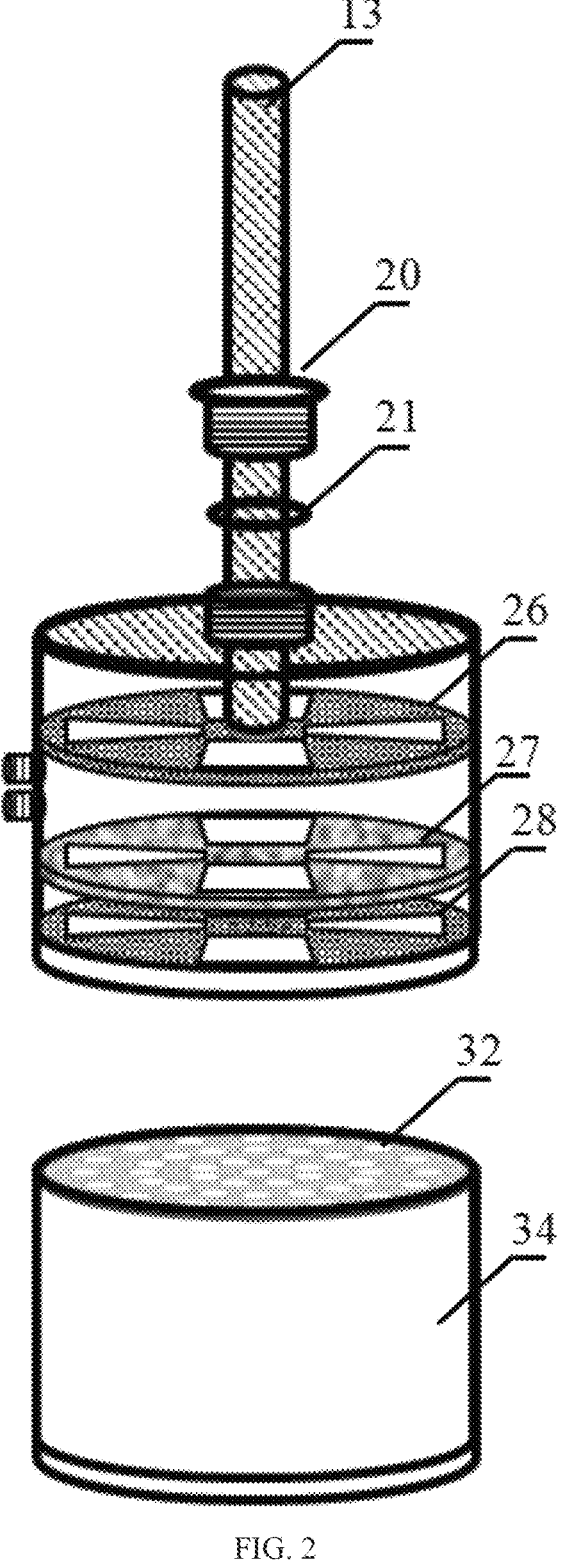
FIG. 2 is a schematic diagram of the structure of the upper chamber and the lower chamber.
Figure 3:
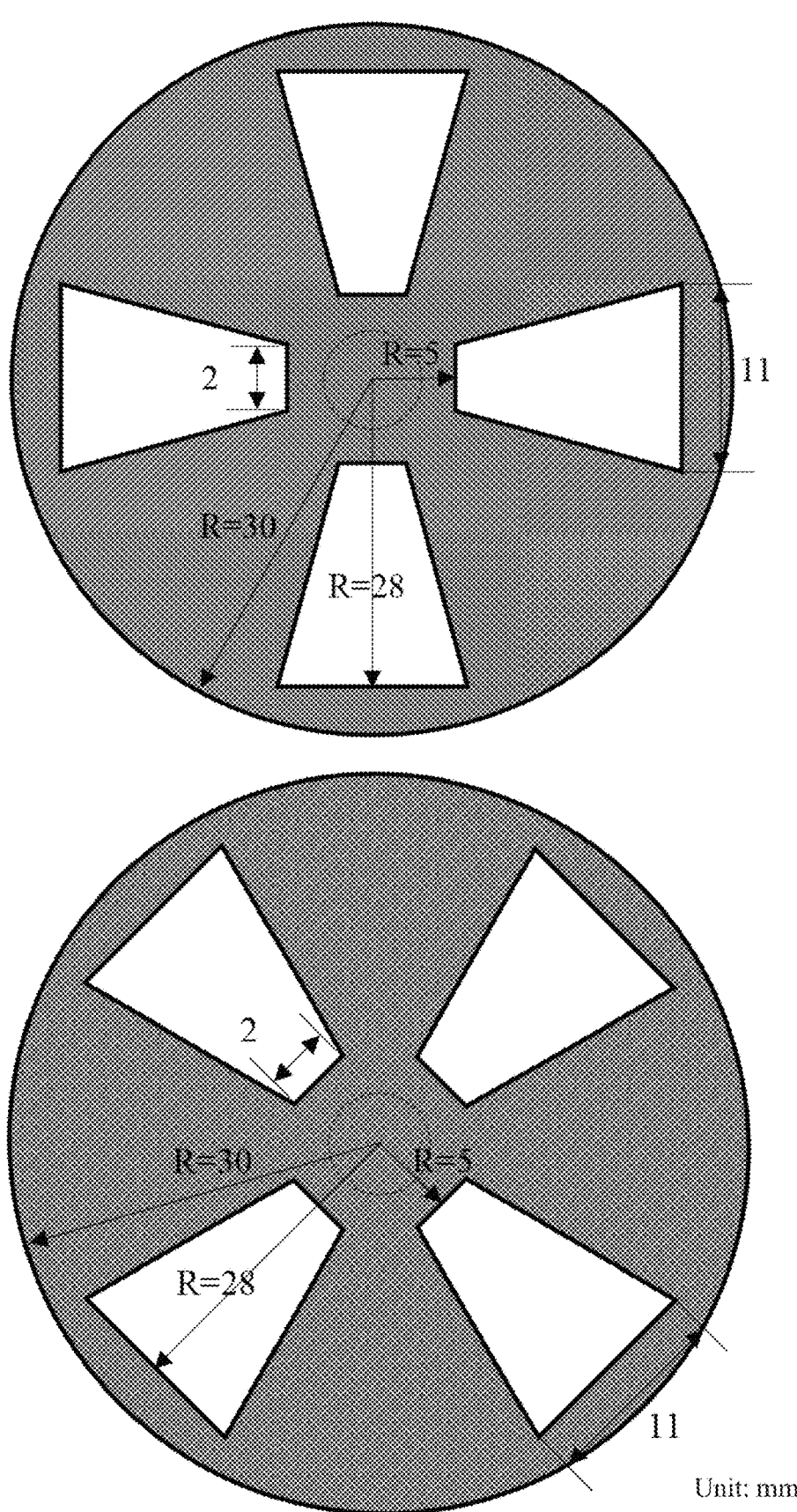
FIG. 3 is a schematic diagram of the openings of the perforated loading plate and the perforated silicone gasket, both of which have the same specifications for the openings.

As shown in FIG. 1-3, the flexible wall device for measuring gas permeability coefficients and gas diffusion coefficients of unsaturated soils: it consists of a gas washing device, a confining pressure-volume change system, a drying-wetting cycle control system and a gas measuring device, the gas washing device includes a high-purity nitrogen cylinder 1, a pressure reducing valve 2, a pressure regulating valve 3 and a steady-flow valve 4 (measurement range 0-100 mL/min); the confining pressure-volume change system includes an air compressor 48, a pressure regulating valve I 49, a pressure regulating valve II 50 and a volume change measuring tube 51; the drying-wetting cycle control system includes a humidity controller 39, a humidity controller valve I 38 and a humidity controller valve II 42; the gas measuring device includes a top lid 17, a cylindrical wall 18, a base 37, an upper chamber 24 and a lower chamber 34, the top lid 17, the cylindrical wall 18 and the base 37 are connected by bolts 12 and nuts 11, and the base 37 has four passages, which are respectively connected to the gas washing device (occupy two passages: air inlet passage 9 and air outlet channel 10), the confining pressure-volume change system (passage: water inlet passage 40), the drying-wetting cycle control system (passages: air outlet passage 10 and base passage 41) and the gas measuring device; between the base 37 and top lid 17 are sequentially arranged from bottom to top as the lower chamber 34, lower perforated plate 32, lower permeable stone 31, sample 30, upper permeable stone 29, upper perforated plate 28, upper chamber 24, and control rod 13.

The top lid 17, the cylindrical wall 18 and the base 37 enclosing a pressure chamber 19; the four passages of the base 37 are respectively air inlet passage 9, air outlet passage 10, water inlet passage 40 and base passage 41, the air inlet end of the air inlet passage 9 is connected to the gas washing device and the air outlet end of the air inlet passage 9 is connected to the upper chamber 24, the nitrogen output from the nitrogen cylinder enters the upper chamber 24 through the air inlet passage 9; the air inlet end of the air outlet passage 10 is connected to the upper chamber 24, the drying-wetting cycle control system, the electronic soap film flowmeter and the capillary tube I; the water inlet end of the water inlet passage 40 is connected to the volume change measuring tube 51 and the water outlet end of the water inlet passage 40 is connected to the pressure chamber 19; the end of the base passage 41 is connected to the lower chamber 34, and the other end of the base passage 41 are respectively connected to the drying-wetting cycle control system and the confining pressure-volume change system.

The high-purity nitrogen cylinder 1 is equipped with the pressure reducing valve 2, the pressure reducing valve 2 is connected to the pressure regulating valve 3 and the steady-flow valve 4 arranged in series, and the steady-flow valve 4 is connected to the air inlet end of the air inlet passage 9 on the base 37. The nitrogen from the high-purity nitrogen cylinder 1 enters the air inlet passage 9 after passing through the pressure reducing valve 2, the pressure regulating valve 3, and the steady-flow valve 4; and the air inlet flow is controlled by adjusting the pressure regulating valve 3 and the steady-flow valve 4.

The humidity controller 39 of the drying-wetting cycle control system is connected to the base passage 41 at one end and the air outlet passage 10 at one other end, the humidity controller valve I 38 is formed between the air outlet passage 10 and the humidity controller 39, and the humidity controller valve II 42 is formed between the base passage 41 and the humidity controller 39. The humidity controller 39 regulates the humidity of the upper chamber 24 through the air outlet passage 10, and the humidity controller 39 regulates the humidity of the lower chamber 34 through the base passage 41, so that the humidity of the upper chamber 24 and the lower chamber 34 are the same.

The output end of the air compressor 48 is connected to the pressure regulating valve I 49 and the pressure regulating valve II 50 set in parallel, an output end of the pressure regulating valve I 49 is connected to one end of the volume change measuring tube 51, one other end of the volume change measuring tube 51 is connected to the water inlet end of the water inlet passage 40 of the base 37, and the water inlet passage 40 is connected to the pressure chamber 19. Apply a constant air pressure to the volume change measuring tube 51 using the pressure regulating valve I 49, so that the liquid inside the volume change measuring tube 51 fills the inside of the pressure chamber 19, and the final confining pressure inside the pressure chamber 19 is equal to the applied constant air pressure.

When measuring the volume change, the drying-induced shrinkage of the sample produces a volume change that causes liquid to flow from the volume change measuring tube 51 into the pressure chamber 19, and similarly, the wetting-induced swelling of the sample produces a volume change that causes water to flow from the pressure chamber 19 into the volume change measuring tube 51, which is used to measure the volume change of the sample by recording the readings from the volume change measuring tube. The output end of the pressure regulating valve II 50 is connected to the base passage 41 of the base 37 in turn via a U-shaped pressure measuring tube 47 (range 0-5 kPa, accuracy 0.01 kPa), a gas sampling port 43 and a capillary tube II 45. The base passage 41 leads to the lower chamber 34. During the gas diffusion coefficient measurement, the pressure regulating valve II 50 is in the closed state, and then open the capillary valve II 44 as well as the capillary valve I 6, so that the gas pressure in both the lower chamber 34 and the upper chamber 24 are equal to the atmospheric pressure. During the gas permeability coefficient measurement, the capillary valve II 44 as well as the capillary valve I 6 are closed, the gas pressure in the lower chamber 34 is increased at the output end of the air compressor 48 by means of the pressure regulating valve II 50, and the upper chamber 24 is connected to the atmosphere by means of the air outlet pipe 23, so that the gas pressure in the upper chamber is equal to the atmospheric pressure.

The exhaust valve 16 and the control rod 13 connected to a perforated loading plate 26 at one end is formed at the top lid 17, the control rod 13 rotatably runs through the top of the top lid 17 and the upper chamber 24, and the perforated loading plate 26 is connected to a lower end of the control rod 13 and is located inside the upper chamber 24; the bottom of the upper chamber 24 is sequentially equipped with the upper permeable stone 29 and the upper perforated plate 28 from bottom to top, a piece of perforated silicone gasket 27 is formed between the upper perforated plate 28 and the perforated loading plate 26, and the opening specifications of the perforated loading plate 26, the perforated silicone gasket 27, and the upper perforated plate 28 are exactly the same, the perforated silicone gasket 27 and the upper perforated plate 28 are tightly bonded and placed according to the overlap of the openings, and the two openings do not block each other; the top of the lower chamber 34 is equipped with the lower perforated plate 32 and the lower permeable stone 31 from bottom to top, a foundation 35 is formed at a bottom of the lower chamber 34, the upper chamber 24 and the lower chamber 34 have the same internal net height.

The control rod 13 seals a sealing ring 115 and the top lid 17 through nut 114, and the control rod 13 seals a sealing ring II 21 and the upper chamber 24 through nut II 20.

The upper chamber 24 is provided with two openings on its side-wall, and the two openings are connected to an air inlet pipe 22 and an air outlet pipe 23, the air inlet pipe 22 is connected to the air inlet passage 9 of the base 37, the air outlet pipe 23 is connected to the humidity controller 39, an electronic soap film flowmeter 8, a capillary tube I 5 in turn through the air outlet passage 10, and a droplet is injected into the aforementioned capillary tube I 5.

The method for measuring gas permeability coefficients and gas diffusion coefficients of unsaturated soils, including the following steps:

Step 1, preparation of sample 30: the soil (silt sand) to be measured is dried, crushed and sieved through a 2 mm sieve, the soil is adjusted to the target moisture content (for example, 22%), and then compacted in layers with molds according to the target dry density (for example, 1.56 g/cm³), and the inter-layer interface is scraped.

Step 2, install the sample 30: place the lower chamber 34, the sample 30, and the upper chamber 24 on the surface of the foundation 35 from bottom to top, and paste a thin layer of Vaseline on the outer walls of the foundation 35, the lower chamber 34 and the upper chamber

24; and then wrap a latex film 33 on the sidewalls of the foundation 35, the lower chamber 34, the sample 30 and the upper chamber 24, and finally fix the two ends of the latex film 33 on the foundation 35 and the upper chamber 24 respectively with O-rings I 36 and O-rings II 25, and then immediately followed by fixing and sealing the cylindrical wall 18, the base 37, and the top lid 17 with nuts 11 and bolts 12; open the exhaust valve 16, adjust the pressure regulating valve I 49, and apply 5 kPa air pressure to the volume change measuring tube 51, so that water flows through the pipeline into the pressure chamber 19, until the exhaust valve 16 discharges water and no air bubbles, close the exhaust valve 16; adjust the pressure regulating valve I 49, and apply 20 kPa confining pressure to the sample 30.

Step 3, flush the upper chamber 24: close all the valves, rotate the control rod 13, so that the openings on the perforated loading plate 26 and the upper perforated plate 28 just misalign with each other, to isolate gas of the upper chamber 24 from entering the sample 30 through the upper perforated plate 28, and then open the high-purity nitrogen cylinder 1 and the valve of electronic soap film flowmeter 7, control the inlet flow rate to 100 ml/min through adjusting the pressure regulating valve 3 and the steady-flow valve 4, and the gas flows into the upper chamber 24 through the air inlet pipe 22, and is discharged into the atmosphere through the air outlet pipe 23; after 8-10 minutes, close the pressure reducing valve 2 of the high-purity nitrogen cylinder 1 and the valve of electronic soap film flowmeter 7 to stop the nitrogen input.

Step 4, open the capillary valve I 6 and capillary valve II 44, so that the gas pressure in the upper chamber 24 and the lower chamber 34 are the same as the atmospheric pressure, and then rotate the control rod 13, so that the perforated loading plate 26 and the upper perforated plate 28 connect with each other through their respective openings, and the gas in the upper chamber 24 can flow through the upper perforated plate 28 into the sample 30, and immediately start the timer, this time t=0, and then determine the concentration of oxygen in the lower chamber 34 over time through the gas sampling port 43, which is connected to the lower chamber 34. For soil samples with a moisture content of 22% by weight, the concentration in the lower chamber 34 shall be measured on an hourly time scale. The concentration of oxygen shall be measured on a time scale of minutes for soil samples with 9% and 18% moisture content by mass obtained by subsequent drying using a humidity controller.

Step 5, the following theoretical equation derived from Fick's law is used to best-fit the oxygen concentration in the lower chamber 34 with respect to time to determine the gas diffusion coefficient $D_p$:

$$D_P = -\frac{3H^2 Lt\left[\ln B - \ln A + \ln\left(\frac{H}{2H + 2L\varepsilon} - \frac{C_t}{C_0}\right)\right]}{3H - L\varepsilon} \quad (1)$$

$$\text{wherein: } A = -\frac{L\varepsilon}{H} - \frac{2L^2\varepsilon^2}{3H^2} \quad (2)$$

$$B = \left(\frac{L\varepsilon}{H} - \frac{L^2\varepsilon^2}{3H^2}\right)\left(\frac{5L\varepsilon}{3H} + 2\right) + \frac{L^3\varepsilon^3}{H^3} + \frac{L^2\varepsilon^2}{H^2} \quad (3)$$

11

12 wherein: t (s) is the time; L is half of the height (m) of the sample; H is the internal net height (m; equal to the internal net height of the lower chamber) of the upper chamber; $C_0$ and $C_t$ are the oxygen concentration ($m^{-3}$ $m^{-3}$) in the lower chamber at the beginning and the oxygen concentration in the lower chamber at the time of t; $\varepsilon$ is the gas-filled porosity of the sample ($m^{-3}$ $m^{-3}$).

Step 6, the measurement of gas permeability coefficient: close the capillary valve I 6 and capillary valve II 44, open the valve of the U-shaped pressure measuring tube 46 and the valve of electronic soap film flowmeter 7, open the air compressor 48, adjust the inlet pressure through the pressure regulating valve II 50 to apply a Table 1 shows as the sample is dried from the initial gravimetric water content of 22% to 9%, the differences between the measurements of rigid wall and flexible wall devices gradually increase. This is due to the fact that the drying of the sample produces volume contraction, so that the influence of the preferential flow of gas along the side wall of the rigid wall device and the sample is gradually increased. The device of the present invention is capable of overcoming the influence of the preferential flow of gas along the side wall, thus achieving the accurate measurement of gas permeability coefficient and diffusion coefficient of unsaturated soils.

| Gravimetric water content (%) | The present invention | | Rigid wall measurement | | Measurement variance (%)[a] | |
|---|---|---|---|---|---|---|
| | Gas permeability coefficient ($m^2$) | Gas diffusion coefficient ($m^2/s$) | Gas permeability coefficient ($m^2$) | Gas diffusion coefficient ($m^2/s$) | Gas permeability coefficient | Gas diffusion coefficient |
| 22 | $8.07 \times 10^{-8}$ | $1.17 \times 10^{-7}$ | $8.32 \times 10^{-8}$ | $1.20 \times 10^{-7}$ | 3.00 | 2.50 |
| 18 | $1.05 \times 10^{-7}$ | $2.40 \times 10^{-7}$ | $1.15 \times 10^{-7}$ | $2.60 \times 10^{-7}$ | 8.70 | 7.69 |
| 9 | $2.35 \times 10^{-7}$ | $8.30 \times 10^{-7}$ | $2.75 \times 10^{-7}$ | $9.30 \times 10^{-7}$ | 14.55 | 10.75 | constant air pressure in the lower chamber 34; after the U-shaped pressure measuring tube (47) readings have stabilized for 2-3 minutes, record the readings from the U-shaped pressure measuring tube 47 and the electronic soap film flowmeter 8.

Step 7, the inlet pressure is changed to obtain the gas flow rate at three different air pressures (for example $2\times 10^{-6}$–$7\times10^{-6}$ $m^3/s$), and the gas permeability coefficient of the soil sample can be calculated according to the following equation derived based on Darcy's law;

$$k_a = \frac{\mu Q h}{S \Delta P} \quad (4)$$

where S is the cross-sectional area of the sample ($m^2$); $\rho$ is the viscosity coefficient of the gas (Pa·s); $\Delta P$ is the pressure difference (Pa) between the two ends of the sample; h is the height of the sample (m); Q is the outflow rate of the gas ($m^3/s$).

Step 8, close the valve of the U-shaped pressure measuring tube 46 and valve of electronic soap film flowmeter 7, open the humidity control valve I 38 and humidity control valve II 42, adjust the humidity controller 39 according to the target moisture content, and control the flow of "dry" gas through the sample 30 and equilibrate it for several days, so that the gravimetric water content of the sample is reduced from the initial 22% to 18% and 9%, and when the gravimetric water content of the sample is reduced to the target value, repeat the steps 4 to 7 to obtain the gas permeability coefficients and the gas diffusion coefficients of the soil samples with different gravimetric water contents. Before and after the change in water content of the sample, the reading of the volume change measuring tub 51 is recorded to obtain the value of the volume change of the sample.

By measuring samples of silty sand with different gravimetric water contents (dry density 1.56 $g/cm^3$), the gas permeability coefficient and diffusion coefficient of unsaturated soil obtained by the device of the present invention and the rigid wall measurement method are compared (Table 1).

a. Measurement variance is defined as:

$$\frac{\left| \text{Measured values of the present invention} - \text{Measured values of the rigid wall device} \right|}{\text{Measured values of the rigid wall device}} \times 100\%$$

Terms applied in any of the above-described technical solutions of the present invention disclosure to denote positional relationships or shapes have a meaning that includes states or shapes that are proximate, analogous, or in close proximity thereto, unless otherwise declared.

Any of the components provided by the present invention may be either assembled from a plurality of individual components or may be an individual component manufactured by a one-piece molding process.

Finally, it should be noted that: the above embodiments are only used to illustrate the technical program of the present invention rather than its limitations; although the invention is described in detail with reference to the better embodiments, the person of ordinary skill in the field should understand that: it is still possible to modify the specific embodiments of the present invention or replace some of the technical features with equivalent ones; without departing from the spirit of the technical program of the present invention, which should be covered by the scope of the technical program of the present invention for the purpose of protection.

What is claimed is:

1. A flexible wall device for measuring gas permeability coefficient and gas diffusion coefficient of unsaturated soil, comprising:
    a gas washing device;
    a confining pressure-volume change system;
    a drying-wetting cycle control system; and
    a gas measuring device;
    wherein the gas washing device comprises a high-purity nitrogen cylinder, a pressure reducing valve, a pressure regulating valve and a steady-flow valve;

wherein the confining pressure-volume change system comprises an air compressor, a first pressure regulating valve, a second pressure regulating valve and a volume change measuring tube;

wherein the drying-wetting cycle control system comprises a humidity controller, a first humidity controller valve and a second humidity controller valve;

wherein the gas measuring device comprises a top lid, a cylindrical wall, a base, an upper chamber and a lower chamber, wherein the top lid, the cylindrical wall and the base are connected by bolts and nuts, and the base has four passages, wherein the four passages are respectively connected to the gas washing device, the confining pressure-volume change system, the drying-wetting cycle control system and the gas measuring device; and wherein between the base and the top lid are sequentially arranged from bottom to top as the lower chamber, a lower perforated plate, a lower permeable stone, a sample, an upper permeable stone, an upper perforated plate, the upper chamber, and a control rod;

wherein the top lid, the cylindrical wall and the base enclosing a pressure chamber;

the four passages of the base are respectively an air inlet passage, an air outlet passage, a water inlet passage and a base passage, wherein an air inlet end of the air inlet passage is connected to the gas washing device, and an air outlet end of the air inlet passage is connected to the upper chamber;

wherein an air inlet end of the air outlet passage is connected to the upper chamber, and an air outlet end of the air outlet passage is connected to the drying-wetting cycle control system;

wherein a water inlet end of the water inlet passage is connected to the volume change measuring tube, and a water outlet end of the water inlet passage is connected to the pressure chamber; and wherein a first end of the base passage is connected to the lower chamber, and a second end of the base passage are respectively connected to the drying-wetting cycle control system and the confining pressure-volume change system.

2. The flexible wall device for measuring gas permeability coefficient and gas diffusion coefficient of unsaturated soil according to claim 1, wherein:

the high-purity nitrogen cylinder is equipped with the pressure reducing valve, the pressure reducing valve is connected to the pressure regulating valve and the steady-flow valve arranged in series, and the steady-flow valve is connected to the air inlet end of the air inlet passage on the base.

3. The flexible wall device for measuring gas permeability coefficient and gas diffusion coefficient of unsaturated soil according to claim 1, wherein:

the humidity controller of the drying-wetting cycle control system is connected to the base passage at a first end and the air outlet passage at a second end, the first humidity controller valve is installed between the air outlet passage and the humidity controller, and the second humidity controller valve is installed between the base passage and the humidity controller.

4. The flexible wall device for measuring gas permeability coefficient and gas diffusion coefficient of unsaturated soil according to claim 1, wherein:

an output end of the air compressor is connected to the first pressure regulating valve and the second pressure regulating valve set in parallel, an output end of the first pressure regulating valve is connected to a first end of the volume change measuring tube, a second end of the volume change measuring tube is connected to the water inlet end of the water inlet passage of the base, and the water inlet passage is connected to the pressure chamber;

an output end of the second pressure regulating valve is connected to the base passage of the base in turn via a U-shaped pressure measuring tube, a gas sampling port and a second capillary tube, the base passage leads to the lower chamber, and the second pressure regulating valve is used to regulate a gas pressure in the lower chamber.

5. The flexible wall device for measuring gas permeability coefficient and gas diffusion coefficient of unsaturated soil according to claim 1, wherein:

a side-wall of the upper chamber is provided with two openings, and the two openings are connected to an air inlet pipe and an air outlet pipe;

the air inlet pipe is connected to the air inlet passage of the base, the air outlet pipe is connected to the humidity controller, an electronic soap film flowmeter and a first capillary tube in turn through the air outlet passage; and a droplet is injected into the first capillary tube.

6. The flexible wall device for measuring gas permeability coefficient and gas diffusion coefficient of unsaturated soil according to claim 1, wherein:

an exhaust valve and the control rod connected to a perforated loading plate at one end are formed at the top lid, wherein the control rod rotatably runs through a top of the top lid and the upper chamber, and the perforated loading plate is connected to a lower end of the control rod and is located inside the upper chamber;

wherein a bottom of the upper chamber is sequentially equipped with the upper permeable stone and the upper perforated plate from the bottom to the top, a piece of perforated silicone gasket is formed between the upper perforated plate and the perforated loading plate, and opening specifications of the perforated loading plate, the perforated silicone gasket, and the upper perforated plate are exactly same, the perforated silicone gasket and the upper perforated plate are tightly bonded and placed according to an overlap of opening parts, and the two openings do not block each other;

a top of the lower chamber is equipped with the lower perforated plate and the lower permeable stone from bottom to top, a foundation is formed at a bottom of the lower chamber, and the upper chamber and the lower chamber have a same internal net height.

7. The flexible wall device for measuring gas permeability coefficient and gas diffusion coefficient of unsaturated soil according to claim 6, wherein:

the control rod seals a first sealing ring and the top lid through a first nut; and the control rod seals a second sealing ring and the upper chamber through a second nut.

8. A method for measuring gas permeability coefficient and gas diffusion coefficient of unsaturated soil, comprising employing the flexible wall device for measuring gas permeability coefficient and gas diffusion coefficient of unsaturated soil according to claim 1, comprising the following steps:

step 1, preparation of sample: the soil to be measured is dried, crushed and sieved through a 2 mm sieve, the soil is adjusted to a target moisture content, and then compacted in layers with molds according to a target dry density, and an inter-layer interface is scraped;

step 2, install the sample: place the lower chamber, the sample, and the upper chamber on a surface of the foundation from bottom to top, and paste a thin layer of Vaseline to outer walls of the foundation, the lower chamber and the upper chamber, and then wrap a latex film on sidewalls of the foundation, the lower chamber, the sample and the upper chamber, and finally fix the two ends of the latex film on the foundation and the upper chamber respectively with first O-rings and second O-rings, and then immediately followed by fixing and sealing the cylindrical wall, the base, and the top lid with nuts and bolts; open the exhaust valve, adjust the first pressure regulating valve, and apply a certain air pressure to the volume change measuring tube, leading to water go through the pipeline into the pressure chamber, until the exhaust valve discharges water and no air bubbles, close the exhaust valve; adjust the first pressure regulating valve, and apply a certain confining pressure (10-20 kPa) to the sample;

step 3, flush the upper chamber: close all the valves, rotate the control rod, so that apertures on the perforated loading plate and the upper perforated plate just misaligned with each other, to isolate gas of the upper chamber from entering the sample through the upper perforated plate, and then open the high-purity nitrogen cylinder and the valve of electronic soap film flowmeter, control the inlet flow rate through an adjustment of the pressure regulating valve and the steady-flow valve, and the gas flows into the upper chamber through the air inlet pipe, and is discharged into the atmosphere through the air outlet pipe; after 8-10 minutes, close the pressure reducing valve of the high-purity nitrogen cylinder and the valve of electronic soap film flowmeter to stop the nitrogen input;

step 4, open the first capillary valve and the second capillary valve, rotate the control rod, so that the perforated loading plate and the upper perforated plate connect with each other through their respective openings, and the gas in the upper chamber flows through the upper perforated plate into the sample, and immediately start the timer, this time t=0, and then determine the concentration of oxygen in the lower chamber over time through the gas sampling port, which is connected to the lower chamber, for the sample with the degree of saturation <85%, an oxygen concentration in the lower chamber is measured in minutes as a time scale, and for the sample with the degree of saturation ≥85%, the oxygen concentration in the lower chamber is measured on a time scale of hours;

step 5, the following theoretical equation was derived from Fick's law and is used to best-fit the oxygen concentration in the lower chamber with respect to time to determine the gas diffusion coefficient $D_p$: wherein:

$$D_P = -\frac{3H^2 Lt\left[\ln B - \ln A + \ln\left(\frac{H}{2H+2L\varepsilon} - \frac{C_t}{C_0}\right)\right]}{3H - L\varepsilon} \quad (1)$$

-continued $$A = -\frac{L\varepsilon}{H} - \frac{2L^2\varepsilon^2}{3H^2} \quad (2)$$

$$B = \left(\frac{L\varepsilon}{H} - \frac{L^2\varepsilon^2}{3H^2}\right)\left(\frac{5L\varepsilon}{3H} + 2\right) + \frac{L^3\varepsilon^3}{H^3} + \frac{L^2\varepsilon^2}{H^2} \quad (3)$$

wherein: t is the time; L is half of a height of the sample; H is the internal net height of the upper chamber; $C_0$ and $C_t$ are the oxygen concentration in the lower chamber at the beginning and the oxygen concentration in the lower chamber at the time of t, respectively; e is the gas-filled porosity of the sample;

step 6, the measurement of gas permeability coefficient: close the first capillary valve and the second capillary valve, open the valve of the U-shaped pressure measuring tube and valve of electronic soap film flowmeter, open the air compressor, adjust the inlet pressure through the second pressure regulating valve to apply a constant air pressure in the lower chamber, when the U-shaped pressure measuring tube readings become stabilized, record the U-shaped pressure measuring tube and electronic soap film flowmeter readings;

step 7, the inlet pressure is changed to obtain the gas flow rates at three different air pressures, and the gas permeability coefficient of the soil sample is calculated according to the following equation derived based on Darcy's law:

$$k_a = \frac{\mu Q h}{S \Delta P} \quad (4)$$

where S is a cross-sectional area of the sample; u is a viscosity coefficient of the gas; ΔP is a pressure difference between the two ends of the sample; h is the height of the sample; Q is an outflow rate of the gas;

step 8, close the valve of the U-shaped pressure measuring tube and valve of electronic soap film flowmeter, open the first humidity control valve and the second humidity control valve, adjust the humidity controller according to the target moisture content, and control the gas flow of constant humidity through the sample, equilibrate for 8-10 days, and repeat step 4 to step 7, the gas permeability coefficients and the gas diffusion coefficients of the soil samples of different moisture contents are obtained; after each drying and wetting cycle, the volume change measuring tube readings are recorded, and the volume change of the sample is obtained.

9. The method for measuring gas permeability coefficient and gas diffusion coefficient of unsaturated soil according to claim 8, wherein:

in the flexible wall device for measuring gas permeability coefficient and gas diffusion coefficient of unsaturated soil, the top lid, the cylindrical wall and the base enclosing a pressure chamber;

the four passages of the base are respectively an air inlet passage, an air outlet passage, a water inlet passage and a base passage, wherein an air inlet end of the air inlet passage is connected to the gas washing device, and an air outlet end of the air inlet passage is connected to the upper chamber;

wherein an air inlet end of the air outlet passage is connected to the upper chamber, and an air outlet end of the air outlet passage is connected to the drying-wetting cycle control system;

wherein a water inlet end of the water inlet passage is connected to the volume change measuring tube, and a water outlet end of the water inlet passage is connected to the pressure chamber; and wherein a first end of the base passage is connected to the lower chamber, and a second end of the base passage are respectively connected to the drying-wetting cycle control system and the confining pressure-volume change system.

10. The method for measuring gas permeability coefficient and gas diffusion coefficient of unsaturated soil according to claim 9, wherein:

in the flexible wall device for measuring gas permeability coefficient and gas diffusion coefficient of unsaturated soil, the high-purity nitrogen cylinder is equipped with the pressure reducing valve, the pressure reducing valve is connected to the pressure regulating valve and the steady-flow valve arranged in series; and the steady-flow valve is connected to the air inlet end of the air inlet passage on the base.

11. The method for measuring gas permeability coefficient and gas diffusion coefficient of unsaturated soil according to claim 9, wherein:

in the flexible wall device for measuring gas permeability coefficient and gas diffusion coefficient of unsaturated soil, the humidity controller of the drying-wetting cycle control system is connected to the base passage at a first end and the air outlet passage at a second end, wherein the first humidity controller valve is installed between the air outlet passage and the humidity controller; and the second humidity controller valve is installed between the base passage and the humidity controller.

12. The method for measuring gas permeability coefficient and gas diffusion coefficient of unsaturated soil according to claim 9, wherein:

in the flexible wall device for measuring gas permeability coefficient and gas diffusion coefficient of unsaturated soil, an output end of the air compressor is connected to the first pressure regulating valve and the second pressure regulating valve set in parallel, an output end of the first pressure regulating valve is connected to a first end of the volume change measuring tube, a second end of the volume change measuring tube is connected to the water inlet end of the water inlet passage of the base, and the water inlet passage is connected to the pressure chamber;

an output end of the second pressure regulating valve is connected to the base passage of the base in turn via a U-shaped pressure measuring tube, a gas sampling port and a second capillary tube, the base passage leads to the lower chamber, and the second pressure regulating valve is used to regulate a gas pressure in the lower chamber.

13. The method for measuring gas permeability coefficient and gas diffusion coefficient of unsaturated soil according to claim 9, wherein:

in the flexible wall device for measuring gas permeability coefficient and gas diffusion coefficient of unsaturated soil, a side-wall of the upper chamber is provided with two openings, and the two openings are connected to an air inlet pipe and an air outlet pipe;

the air inlet pipe is connected to the air inlet passage of the base, the air outlet pipe is connected to the humidity controller, an electronic soap film flowmeter and a first capillary tube in turn through the air outlet passage; and a droplet is injected into the first capillary tube.

14. The method for measuring gas permeability coefficient and gas diffusion coefficient of unsaturated soil according to claim 9, wherein:

in the flexible wall device for measuring gas permeability coefficient and gas diffusion coefficient of unsaturated soil, an exhaust valve and the control rod connected to a perforated loading plate at one end are formed at the top lid, wherein the control rod rotatably runs through a top of the top lid and the upper chamber, and the perforated loading plate is connected to a lower end of the control rod and is located inside the upper chamber;

wherein a bottom of the upper chamber is sequentially equipped with the upper permeable stone and the upper perforated plate from the bottom to the top, a piece of perforated silicone gasket is formed between the upper perforated plate and the perforated loading plate, and opening specifications of the perforated loading plate, the perforated silicone gasket, and the upper perforated plate are exactly same, the perforated silicone gasket and the upper perforated plate are tightly bonded and placed according to an overlap of opening parts, and the two openings do not block each other; and a top of the lower chamber is equipped with the lower perforated plate and the lower permeable stone from bottom to top, a foundation is formed at a bottom of the lower chamber, and the upper chamber and the lower chamber have a same internal net height.

15. The method for measuring gas permeability coefficient and gas diffusion coefficient of unsaturated soil according to claim 14, wherein:

in the flexible wall device for measuring gas permeability coefficient and gas diffusion coefficient of unsaturated soil, the control rod seals a first sealing ring and the top lid through a first nut; and the control rod seals a second sealing ring and the upper chamber through a second nut.

* * * * *